US00PP28403P3

(12) United States Plant Patent
Uchneat

(10) Patent No.: US PP28,403 P3
(45) Date of Patent: Sep. 19, 2017

(54) *DIERVILLA* PLANT NAMED 'G2X885411'

(50) Latin Name: *Diervilla splendens*
Varietal Denomination: G2X885411

(71) Applicant: Michael Uchneat, Bellefonte, PA (US)

(72) Inventor: Michael Uchneat, Bellefonte, PA (US)

(73) Assignee: Garden Genetics LLC, Bellefonte, PA (US)

( * ) Notice: Subject to any disclaimer, the term of this patent is extended or adjusted under 35 U.S.C. 154(b) by 28 days.

(21) Appl. No.: 14/756,867

(22) Filed: Oct. 22, 2015

(65) Prior Publication Data

US 2017/0118891 P1 Apr. 27, 2017

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Cassandra Bright

(57) ABSTRACT

A new and distinct *Diervilla* cultivar named 'G2X885411' is disclosed, characterized by dense branching, red Fall foliage, burgundy new growth and distinctive red seed pods. The new variety is a *Diervilla*, normally produced as an outdoor garden or container plant.

2 Drawing Sheets

Latin name of the genus and species: *Diervilla splendens*.
Variety denomination: 'G2X885411'.

BACKGROUND OF THE INVENTION

The new *Diervilla* cultivar is a product of a planned breeding program conducted by the inventor, Michael Uchneat in Bellefonte, Pa. The objective of the breeding program was to produce new low maintenance landscape plants using native plant species. The open pollination resulting in this new variety was made during August of 2009.

The new *Diervilla* 'G2X885411' resulted from an open pollination in which seed was collected from an unpatented proprietary seedling referred to as '3349-4'. Multiple proprietary varieties of *Diervilla* were present in the field, making accurate identification of the pollen parent impossible. The new variety was identified as a potentially interesting selection Sep. 1, 2011, at a research nursery in Bellefonte, Pa.

Asexual reproduction of the new cultivar 'G2X885411' by vegetative terminal cuttings was first performed during 2011 at research greenhouse in Bellefonte, Pa. Subsequent propagation has shown that the unique features of this cultivar are stable and reproduced true to type in at least 4 successive generations.

SUMMARY OF THE INVENTION

The cultivar 'G2X885411' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G2X885411' These characteristics in combination distinguish 'G2X885411' as a new and distinct *Diervilla* cultivar:

1. Burgundy foliage, especially in new growth.
2. Red Fall foliage color.
3. Dense basal branch development.
4. Vigorous upright growth habit, branches cascading with maturity.
5. Distinctive red seed pods.
6. Plants more compact and better branched than wild species.

PARENT COMPARISON

Plants of the new cultivar 'G2X885411' are similar to plants of the seed parent, in most horticultural characteristics, however, plants of the new cultivar 'G2X885411' differ in the following:

1. Distinctive red seed pods, not found on the seed parent.
2. Red Fall foliage color, the seed parent does not exhibit red Fall color.
3. Burgundy new growth and foliage, foliage and new growth of the seed parent are green.

COMMERCIAL COMPARISON

Plants of the new cultivar 'G2X885411' can also be compared to the known variety *Diervilla ssessifolia*. The varieties are similar in most horticultural characteristics; however 'G2X885411' differs in the following:

1. Distinctive red seed pods, not found on this comparator.
2. Red Fall foliage color, this comparator does not exhibit red Fall color.
3. Burgundy new growth and foliage, foliage and new growth of this comparator are green.
4. Dense branching, plants of this comparator branch loosely and open.

BRIEF DESCRIPTION OF THE PHOTOGRAPHS

Figure 1:
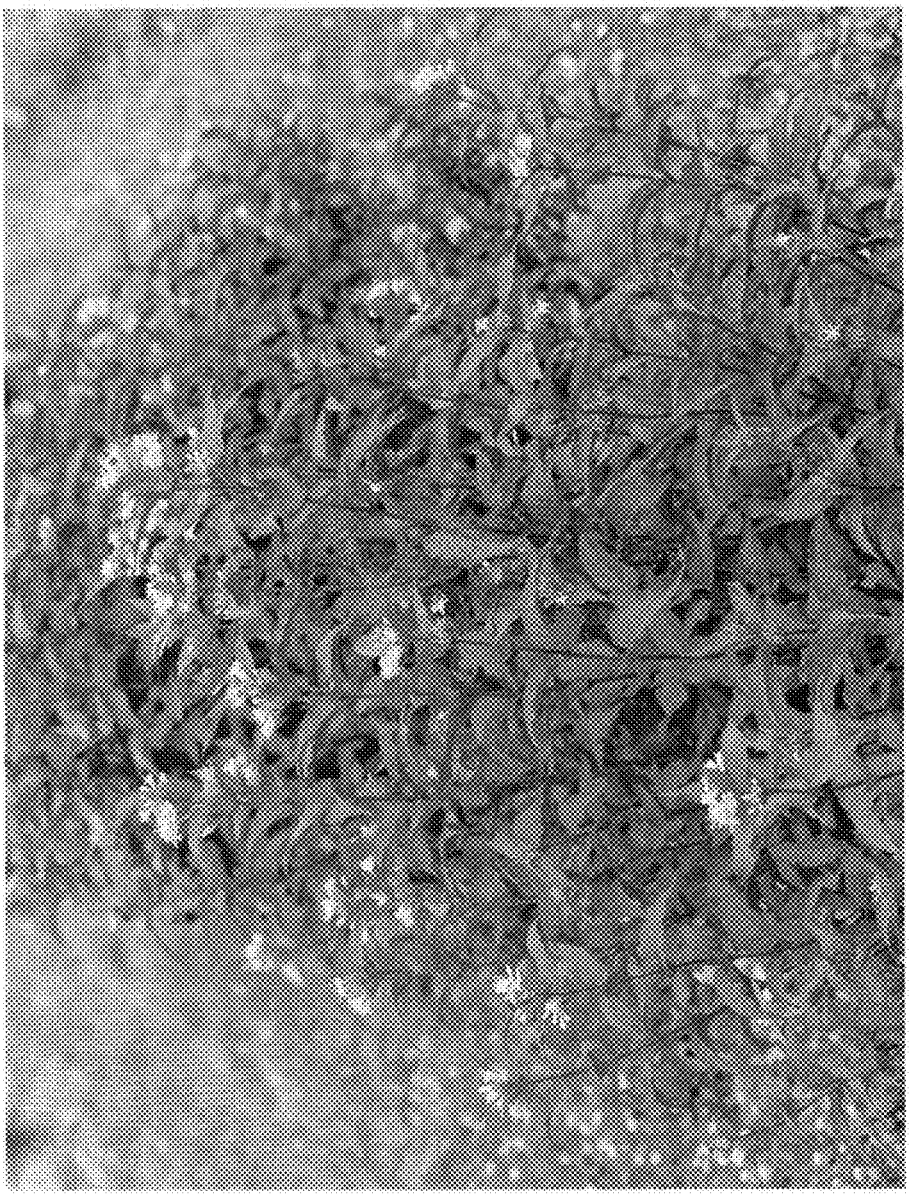

The accompanying photograph in FIG. 1 illustrates in full color a typical 2 year old plant, with burgundy new foliage of 'G2X885411' grown in the ground.

Figure 2:
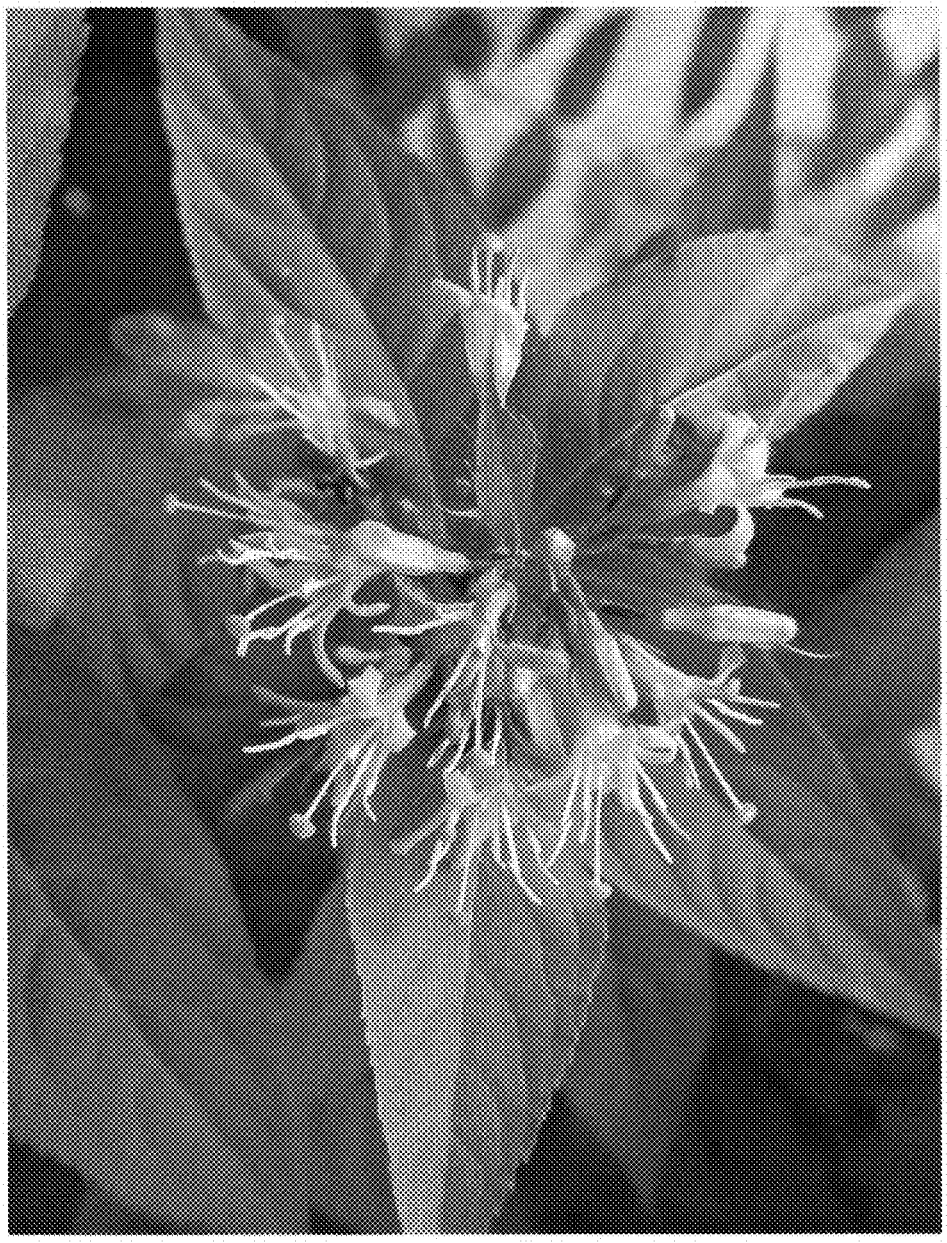

FIG. 2 illustrates in full color a typical inflorescence and green foliage of 'G2X885411' grown outdoors in Grand Haven, Minn., in a garden setting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'G2X885411' plants grown in a poly house in Grand Haven, Minn. This occurred during June of 2014. The plants were between 2 and 3 years old. The growing temperature ranged from 18° C. to 27° C. during the day, and 5° to 10° C. at night. Measurements and numerical values represent averages of typical plant types.

Botanical classification: *Diervilla splendens* 'G2X885411'.

PROPAGATION

Time to initiate roots: About 10 to 21 days at approximately 78° F.

Root description: Between fleshy and fibrous, moderately dense and moderately freely branching. Roots brown, not accurately measured with R.H.S. chart.

Time to produce a liner: About 35 to 42 days at 74° F.

PLANT

Plant type: Shrub perennial.

Age of plant described: Approximately 2 to 3 years old.

Pot size of plant described: 3 gallon pot.

Growth habit: Strong.

Overall plant shape: Rounded.

Height: Approximately 82 cm.

Plant spread: Approximately 82 cm.

Growth rate: Moderate.

Plant vigor: Moderate.

Branching characteristics: Basal, pinching required.

Length of primary lateral branches: Approximately 66-72 cm.

Diameter of lateral branches: Approximately 5-7 mm.

Quantity of lateral branches: 40.

Stem:

- *Appearance*.—Quadrangle, with rounded edges.
- *Aspect/angle*.—45-90° (some very upright).
- *Strength*.—Moderate.
- *Stem pubescence*.—Yes.
- *Stem color*.—New Growth: Near RHS Yellow-Green 144B. Mature growth: Near RHS both Greyed-red 178A and Greyed-red 178B.
- *Other stem characteristics*.—Color underneath mature stem skin is Near RHS Yellow-green 145A.

Internode length: Average range 4.5 cm.

FOLIAGE

Leaf:

- *Arrangement*.—Opposite.
- *Average length*.—Approximately 9-13 cm.
- *Average width*.—Approximately 4-5 cm.
- *Shape of blade*.—Lanceolate.
- *Apex*.—Acuminate.
- *Base*.—Obtuse.
- *Margin*.—Serrulate. Leaf Margins are slightly Greyed-Orange 176A.
- *Texture of top surface*.—Smooth, silky.
- *Texture of bottom surface*.—Smooth, slightly ribbed due to veins.
- *Pubescence*.—None.
- *Color*.—New growth foliage upper side: Near RHS Greyed-Red 178A. New growth foliage under side: Near RHS Greyed-orange 176A. Young foliage upper side: Tip Near RHS Yellow-green 147A and Greyed-orange 176A. Below tip near RHS Green 137C. Young foliage under side: Near RHS Yellow-green 147B. Mature foliage upper side: Near RHS Yellow-green 147A. Summer matures leaves to Near RHS Greyed-Orange 166B. Mature foliage under side: Near RHS Green 139C. Summer matures to Near RHS Greyed-green 191A underlying of Greyed-purple 184A.
- *Venation*.—Type: Pinnate. Venation color upper side: Young growth: Near RHS Greyed-orange 176A. Mature Growth: Near RHS Greyed-orange 176B. Venation color under side: Near RHS Yellow-green 147C with specks of Greyed-orange 174A.
- *Petiole*.—Average Length: Approximately 4 mm. Diameter: Approximately 2-3 mm. Petiole color upper side: Near RHS Yellow-green 146C with slight overlay of Greyed-orange 176B. Petiole color lower side: Near RHS Yellow-green 146C with slight overlay of Greyed-orange 176B. Petiole Texture: Canaliculate.

Other characteristics: Good foliage durability to stresses.

FLOWER

Natural flowering season: Spring to mid-Summer.

Inflorescence type and habit: Cyme.

Quantity of flowers per inflorescence: 3-8.

Quantity of flowers per lateral stem: 30-40.

Quantity of flowers per plant: 100-200.

Individual flowers:

- *Flowering habit*.—Terminal.
- *Flower form*.—Perfect, tubular.
- *Flower aspect*.—Upright.
- *Flower shape*.—Tubular.
- *Size*.—Diameter: Approximately 1-1.5 cm. Flower throat Diameter: Approximately 4 mm. Flower tube Diameter: Approximately 2 mm. Flower Depth: Approximately 1 cm.
- *Persistence*.—Self-cleaning.
- *Fragrance*.—None.

Petal:

- *Petal arrangement*.—Whorl.
- *Number of petals per flower*.—5.
- *Petal appearance*.—Smooth to velvet-like (slightly pubescent).
- *Petal shape*.—Oblong.
- *Tip shape*.—Obovate.
- *Length*.—1 cm from throat.
- *Width*.—2 mm.
- *Texture*.—Upper: Smooth. Lower: Smooth. Tube texture: Smooth. Throat texture: Smooth.

Petal color:

*When opening*.—Upper surface: Near RHS Yellow-green 151C. Lower surface: Near RHS Yellow-green 151C.

*Fully opened*.—Upper surface: Near RHS Greyed-orange 172A. Lower surface: Near RHS Yellow-green 153D. Flower tube color: Near RHS Yellow-green 151C. Flower throat color: Near RHS Yellow-green 151B.

*Fading*.—Upper surface: Near RHS Greyed-orange 165B.

Petaloids: None present.

Bud:

*Shape*.—Oblong.
*Length*.—1.5 cm.
*Diameter*.—4-5 mm.
*Color*.—Near RHS Yellow-green 145A to Yellow-green 151A.

Sepals:

*Appearance*.—Thin and spikey.
*Arrangement*.—Whorl.
*Shape*.—Subulate.
*Length*.—Approximately 3 mm.
*Width*.—Approximately 0.5-1 mm.
*Margin*.—Entire.
*Base*.—Tapered.
*Tip*.—Acuminate.
*Number*.—5.
*Color*.—Near RHS Yellow-Green 144B.

Calyx shape: Whorl.

Peduncle:

*Length*.—10 mm.
*Diameter*.—1 mm.
*Color*.—Near RHS Yellow-green 144A.
*Orientation*.—30-45°.
*Strength*.—Moderate.
*Texture*.—Smooth.

Pedicel:

*Length*.—10 mm.
*Diameter*.—1 mm.
*Angle*.—30-45°.
*Strength*.—Moderate.
*Texture*.—Smooth.
*Color*.—Near RHS Yellow-green 144A.

REPRODUCTIVE ORGANS

Stamens:

*Number*.—5.
*Filament length*.—Approximately 1 cm.
*Filament color*.—Near RHS Yellow-green 145C.

Anthers:

*Shape*.—Linear.
*Length*.—4 mm.
*Color*.—Near RHS Yellow-orange 17A.
*Pollen*.—Little-moderate.
*Pollen color*.—Near RHS Yellow-orange 17A.

Pistil:

*Number*.—1.
*Length*.—1.5 cm.
*Style*.—Length: 1.5 cm. Color: Near RHS yellow-green 144B.
*Stigma*.—Shape: Round. Color: Near RHS Yellow-green 144B. Ovary color: Near RHS Yellow-Green 144B.

OTHER CHARACTERISTICS

Garden performance: Very good performance in the garden, resistant to typical environmental stresses such as wind, sun and extreme temperatures.

Disease/pest resistance: Good resistance to Disease.

Temperature tolerance: The new variety tolerates temperatures between −29 to 35 ° C.

What is claimed is:

1. A new and distinct cultivar of *Diervilla* plant named 'G2X885411' as herein illustrated and described.

* * * * *